US00PP26972P3

(12) United States Plant Patent
Bell

(10) Patent No.: US PP26,972 P3
(45) Date of Patent: Jul. 26, 2016

(54) ***VACCINIUM* HYBRID PLANT NAMED 'RIDLEY 3402'**

(50) Latin Name: ***Vaccinium* hybrid**
Varietal Denomination: Ridley 3402

(71) Applicant: Mountain Blue Orchards Pty Ltd., Lindendale (AU)

(72) Inventor: Ridley Bell, Lindendale (AU)

(73) Assignee: BLUE MOUNTAIN ORCHARDS PTY LTD, Lindendale, NSW (AU)

( * ) Notice: Subject to any disclaimer, the term of this patent is extended or adjusted under 35 U.S.C. 154(b) by 87 days.

(21) Appl. No.: 14/544,201

(22) Filed: Dec. 9, 2014

(65) Prior Publication Data

US 2015/0163973 P1 Jun. 11, 2015

Related U.S. Application Data

(60) Provisional application No. 61/963,659, filed on Dec. 10, 2013.

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette Para
(74) *Attorney, Agent, or Firm* — Hahn Loeser & Parks, LLP

(57) ABSTRACT

A new and distinct cultivar of *Vaccinium* hybrid plant named 'Ridley 3402', characterized by its combination of upright to semi-upright plant growth habit and strong plant growth vigor, evergreen foliage, early to mid-season flowering and fruiting, medium fruit size, moderately firm fruit with a dry picking scar suited to handling, attractive dark blue fruit color and small picking scar.

11 Drawing Sheets

Latin name of genus and species: *Vaccinium* hybrid.
Variety denomination: 'Ridley 3402'.

BACKGROUND OF THE INVENTION

The present invention relates to a new and distinct perennial variety of *Vaccinium* hybrid (Southern Highbush Blueberry), which has been given the variety denomination of 'Ridley 3402'. Its market class is that of a fruiting plant. 'Ridley 3402' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2007 from the controlled pollination of seed parent 'S03-40-02' (unpatented) with pollen parent 'S03-09-01A' (unpatented). The new cultivar was discovered and selected as a single plant within a population of 100 resulting *Vaccinium* hybrid plants from this controlled pollination in 2009 in a commercial field plantation environment at Lindendale, New South Wales, Australia. Selection criteria were a combination of strong plant growth vigor, low chilling requirement, early to medium time of flowering, upright to semi-upright plant growth habit, firm fruit suited to handling, desirable tasting berries and small picking scar. The selection was subsequently evaluated for a number of years at the commercial farms at Lindendale, New South Wales, Australia.

Asexual reproduction of the new cultivar by cutting propagation since 2009 at Lindendale, New South Wales, Australia has demonstrated that the new cultivar reproduces true to type with all of the characteristics, as herein described, firmly fixed and retained through successive generations of such asexual propagation.

The new variety has been primarily compared to the variety 'Ridley 0501' (unpatented). In Lindendale, New South Wales, Australia the plant growth vigor of 'Ridley 3402' is classified as strong whereas the plant growth vigor of 'Ridley 0501' is medium. The berry shape in longitudinal section of 'Ridley 3402' is oblate whereas berry shape in longitudinal section of 'Ridley 0501' is round. The berry diameter of calyx basin of 'Ridley 3402' is medium whereas 'Ridley 0501' is large. The time of beginning of flowering of 'Ridley 3402' is classified as 'early' whereas the time of beginning of flowering of time of 'Ridley 0501' is classified as 'very early'. The intensity of bloom of the berry skin of 'Ridley 3402' is strong whereas 'Ridley 0501' is medium. The berry firmness of 'Ridley 3402' is medium whereas 'Ridley 0501' is medium to firm. The berry sweetness of 'Ridley 3402' is 'medium to high' whereas 'Ridley 0501' is low to medium. This combination of vegetative and fruiting attributes results in 'Ridley 3402' being a desirable and distinctive variety for commercial production.

SUMMARY OF THE INVENTION

Selection criteria was a combination of strong plant growth vigor, low chilling requirement, early to medium time of flowering, upright to semi-upright plant growth habit, firm fruit suited to handling, desirable tasting berries and small picking scar The following characteristics of the new cultivar have been repeatedly observed and can be used to distinguish 'Ridley 3402' as a new and distinct cultivar of *Vaccinium* hybrid plant:

1. strong plant growth vigor
2. upright to semi-upright plant growth habit
3. early to medium timing of beginning of flowering
4. early to medium timing of fruit ripening 5. dark blue berry color
6. picking scar is dry Plants of the new cultivar differ from plants of the seed parent 'S03-40-02' primarily in strong plant growth vigor, strong berry skin bloom intensity and medium berry diameter whereas the seed parent has medium plant growth vigor, very strong berry skin bloom intensity and large berry diameter. Plants of the new cultivar differ from plants of the pollen parent 'S03-09-01A' primarily in strong plant growth vigor and an upright to semi-upright plant growth habit whereas the pollen parent has medium plant growth vigor and a semi-upright plant growth habit.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ridley 3402'.

DETAILED BOTANICAL DESCRIPTION

Figure 1:
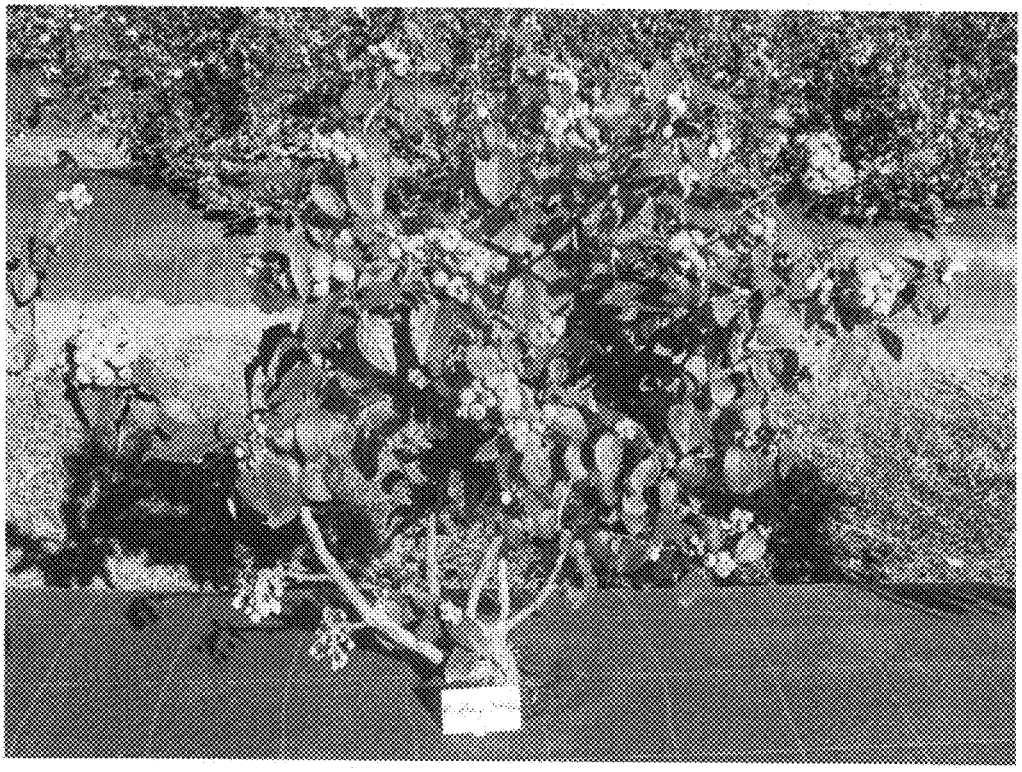
FIG. 1 illustrates a 'Ridley 3402' in a commercial field planting.
Figure 2:
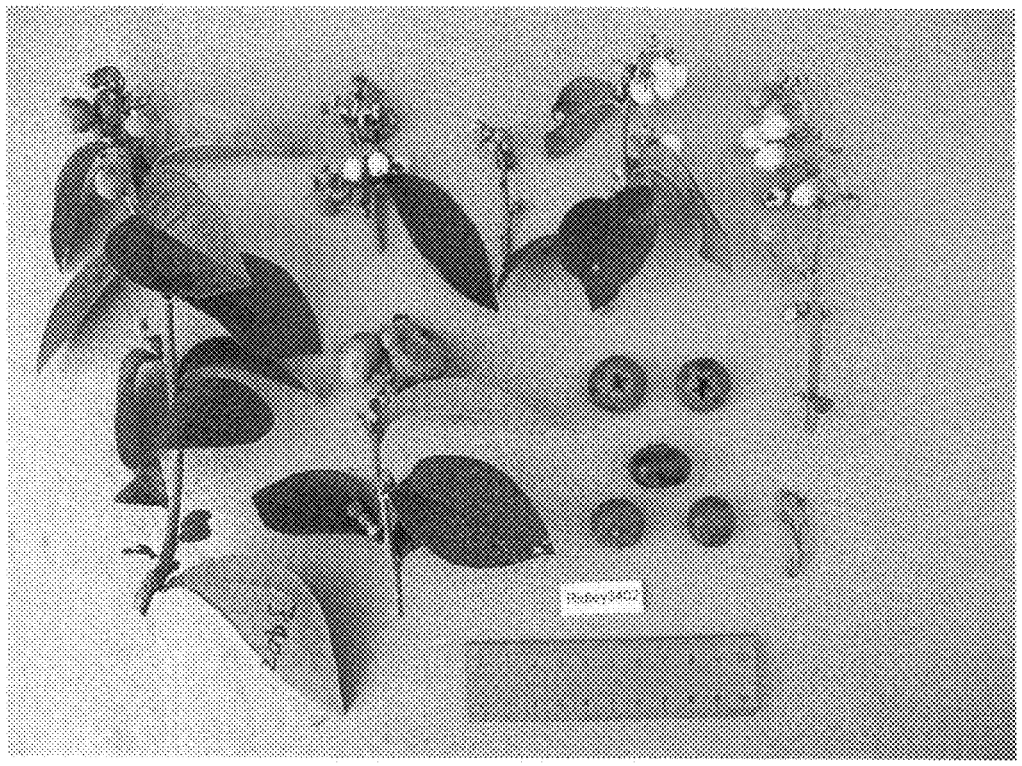
FIG. 2 illustrates 'Ridley 3402' leaf, flower and berry detail.
Figure 3:
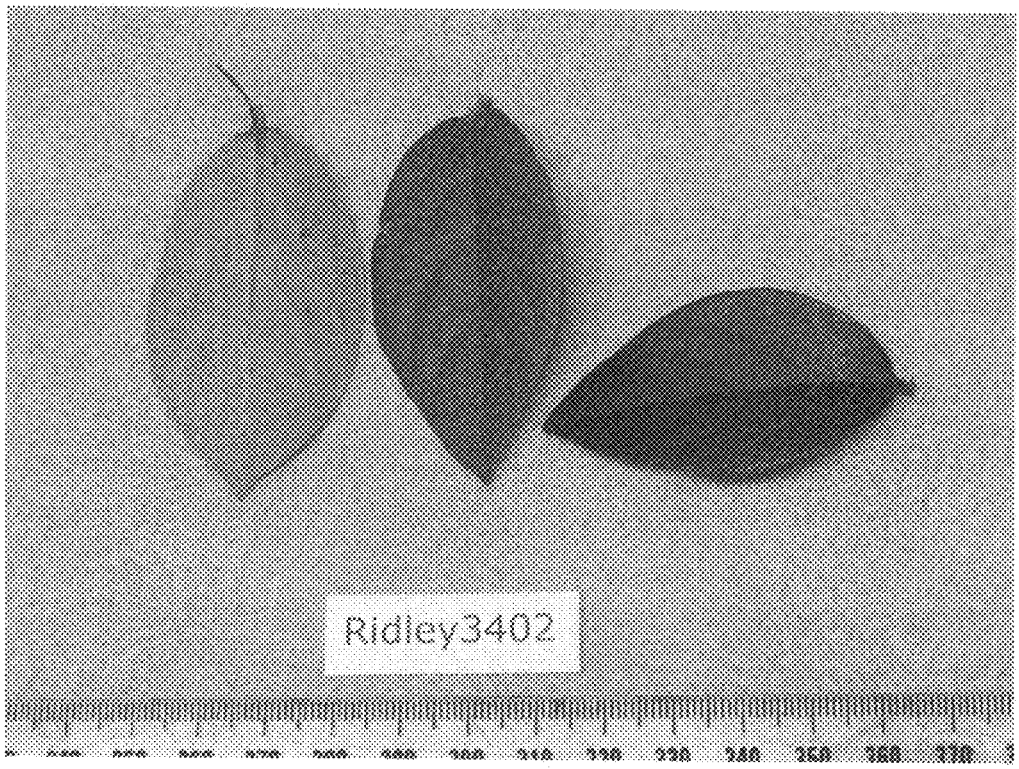
FIG. 3 illustrates 'Ridley 3402' leaf detail.
Figure 4:
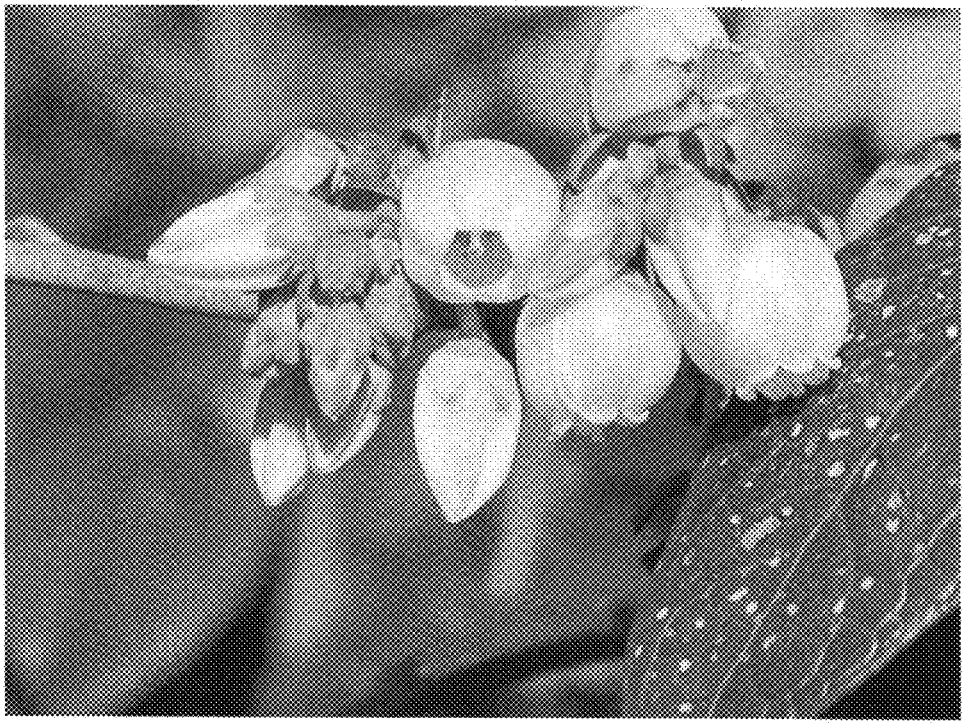
FIG. 4 illustrates 'Ridley 3402' flowering.
Figure 5:
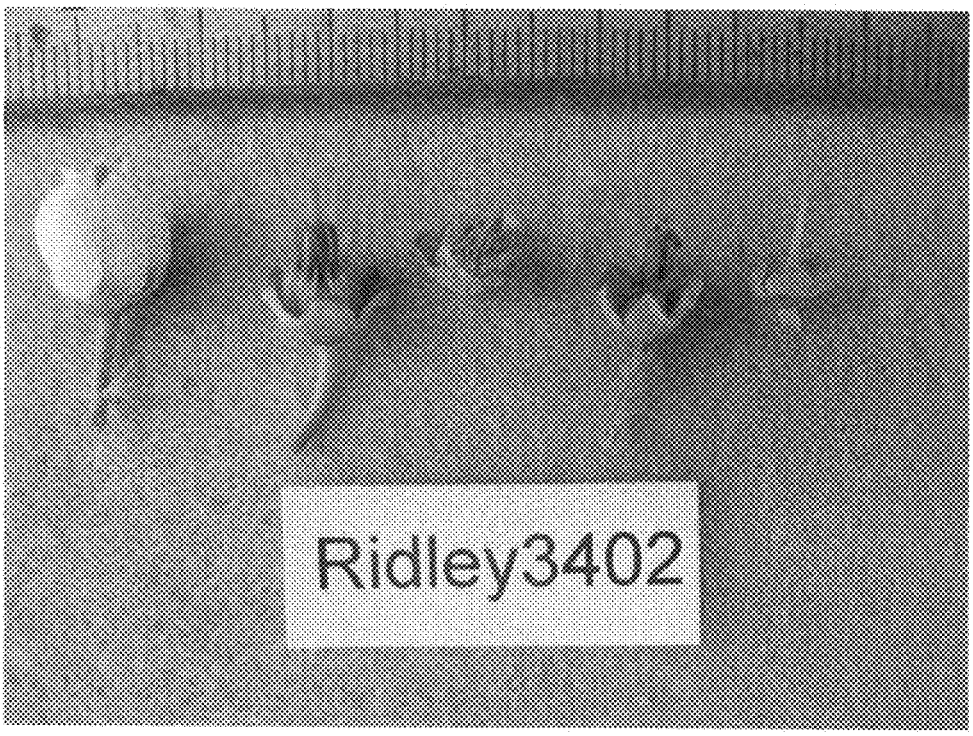
FIG. 5 illustrates 'Ridley 3402' flowering detail.
Figure 6:
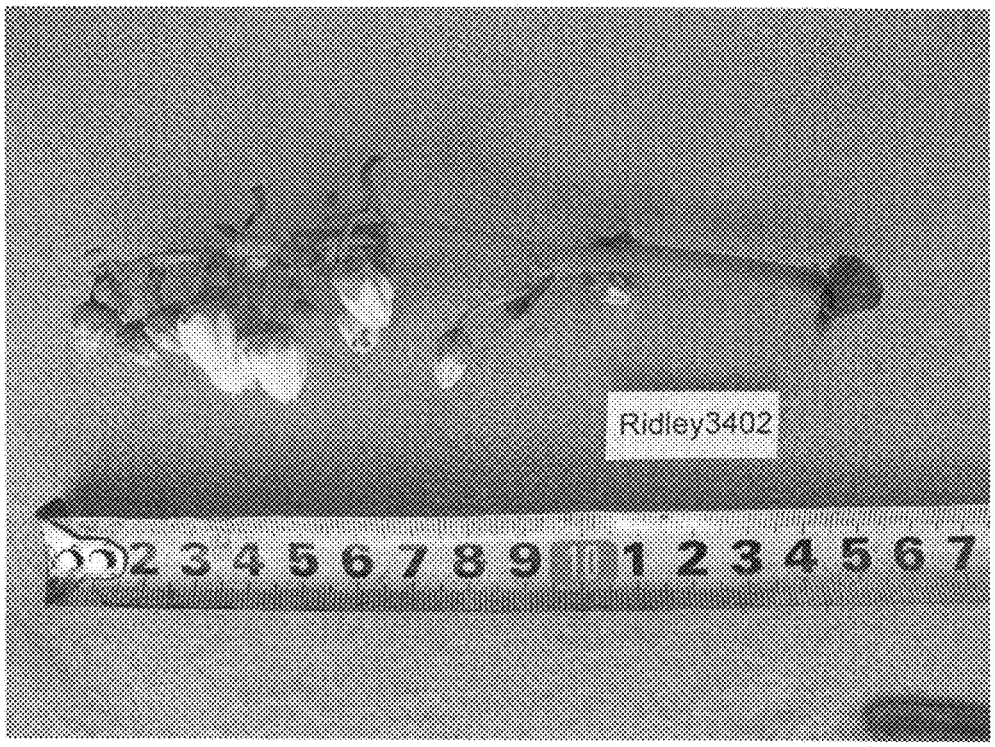
FIG. 6 illustrates 'Ridley 3402' inflorescence on current season shoot.
Figure 7:
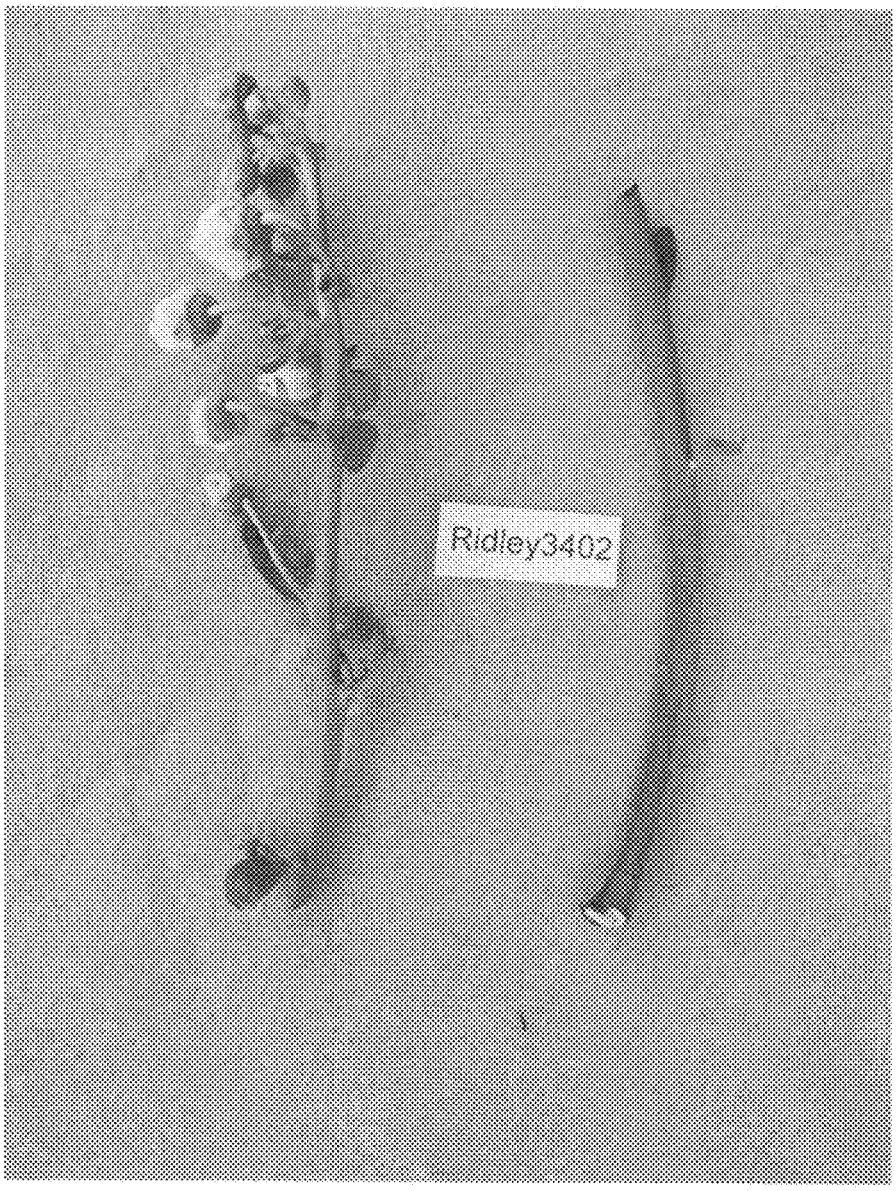
FIG. 7 illustrates 'Ridley 3402' inflorescence on a water shoot.
Figure 8:
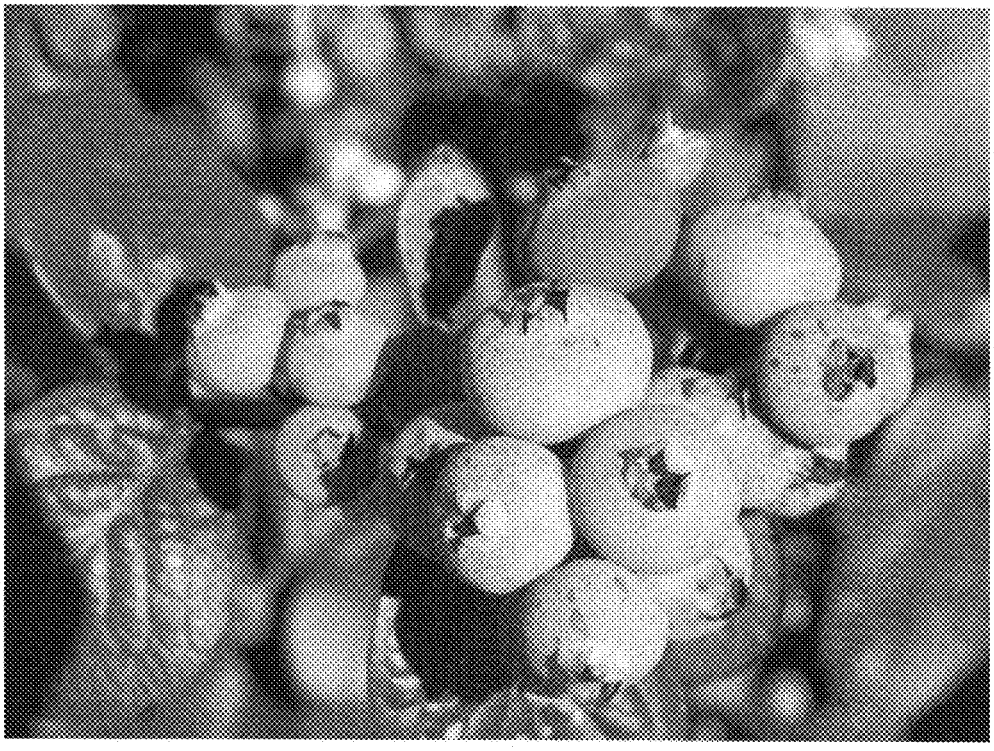
FIG. 8 illustrates 'Ridley 3402' fruit cluster.
Figure 9:
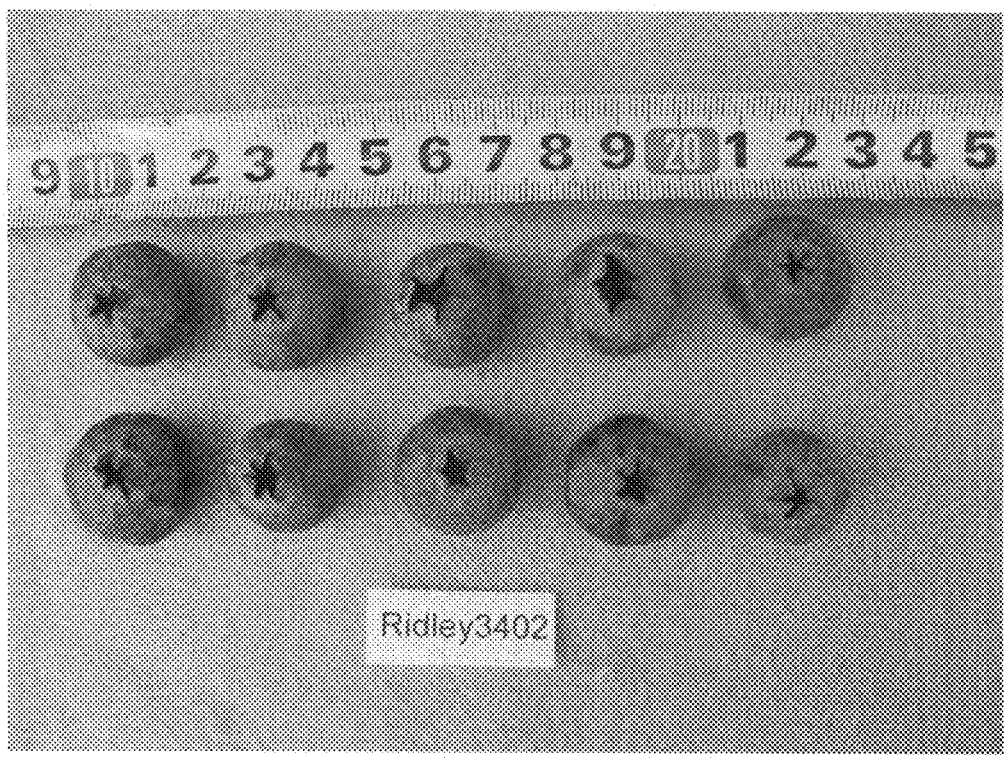
FIG. 9 illustrates 'Ridley 3402' fruit detail.
Figure 10:
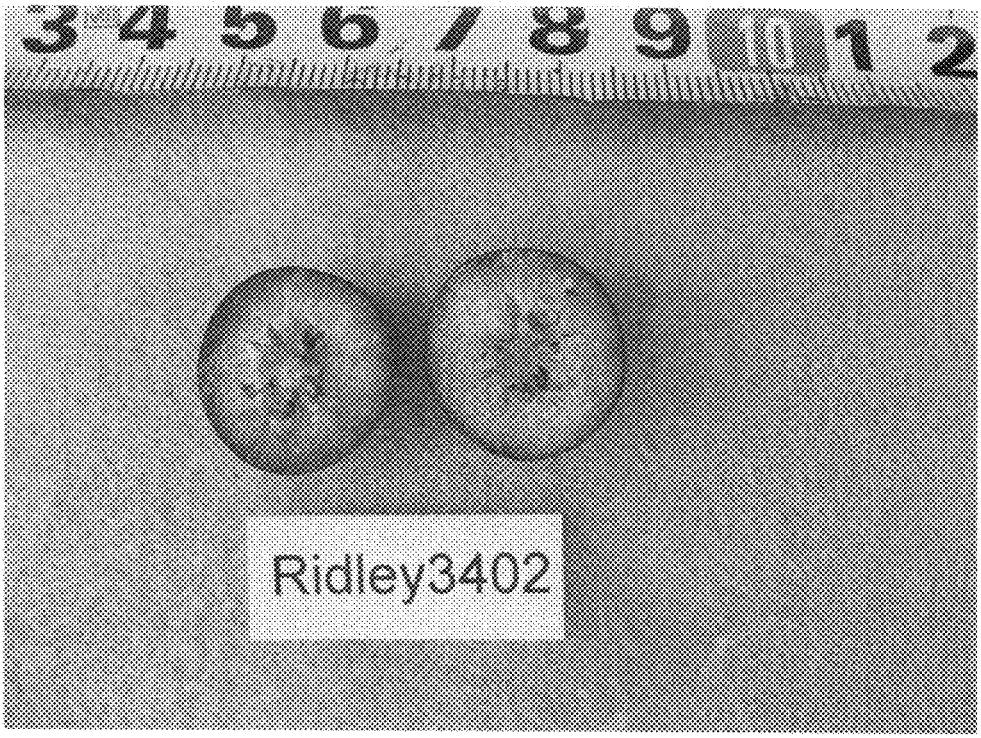
FIG. 10 illustrates 'Ridley 3402' fruit cross section.
Figure 11:
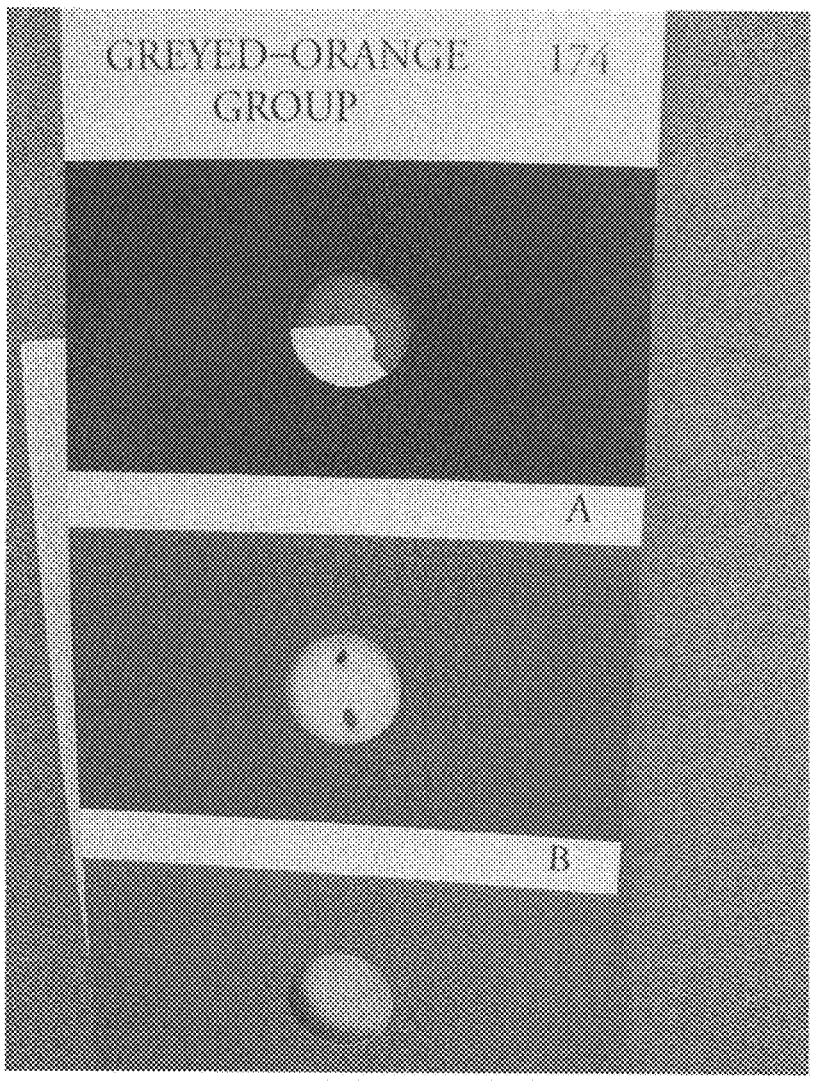
FIG. 11 illustrates 'Ridley 3402' seed color.

The following is a detailed botanical description of a new and distinct variety of a *Vaccinium* hybrid ornamental plant known as 'Ridley 3402'. Plant observations were made on plants grown in Lindendale, New South Wales, Australia. Unless indicated otherwise, the descriptions disclosed herein are based upon observations made in October 2014 of mature 'Ridley 3402' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'Ridley 3402' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on *The Royal Horticultural Society Color Chart,* of The Royal Horticultural Society, London, 2007 edition.

Botanical classification: *Vaccinium* hybrid cultivar 'Ridley 3402'.

Parentage:

*Parents.*—Seed parent 'S03-40-02' (unpatented). Pollen parent 'S03-09-01A' (unpatented).

Plant:

*Growth habit.*—Upright to semi-upright.

*Growth vigor.*—Is strong.

*Plant height.*—Is approximately 2.0 m.

*Plant width.*—Is approximately 1.2 m.

*Flower bud density.*—Is medium.

*Twigginess.*—Is low.

*Time of beginning of flowering.*—Is early to medium (begins mid May; peaks mid August) when grown as an evergreen in Australia.

*Time of fruit ripening.*—Is early to medium (begins early to mid July; peaks early to mid October) when grown as an evergreen in Australia.

Stem:

*Suckering tendency.*—Plants typically have 5-7 major canes per plant from a base 30 cm in diameter on 6 year old plants.

*Canes.*—Erect to semi-erect with moderate branching; color greyed orange 198C; 2 year old cane diameter 12 mm, colored greyed orange 177B, some flaking of bark, new growth (immature shoot) color yellow green 144A with occasional anthocyanin coloration grayed orange 177B, water shoots stem color yellow green 144A with occasional anthocyanin coloration grayed red 178A to grayed purple 183A, current season wood diameter 3-4 mm, colored yellow green 144C. Internode length on strong, new shoots 15-20 mm.

*Fruiting wood.*—Numerous twigs to 12 cm in length.

*Surface texture of new wood.*—Smooth.

Fully developed leaf:

*Length.*—Medium to long 75-90 mm.

*Width.*—Medium to broad 35-40 mm.

*Shape.*—Elliptic.

*Color of upper surface.*—Yellow green 147A.

*Color of lower surface.*—Yellow green 147C.

*Intensity of color.*—Medium.

*Margin.*—Entire.

*Undulation of margin.*—Weak.

*Pubescence of upper side.*—Absent.

*Pubescence of lower side.*—Absent.

*Cross sectional profile.*—Flat.

*Longitudinal profile.*—Straight.

*Attitude.*—Broad acute to horizontal.

*Shape of apex.*—Is acuminate.

*Shape of base.*—Is obtuse.

Inflorescence:

*Length of peduncle.*—To 12 mm.

*Length of pedicel.*—Long 5-7 mm.

*Number of flowers per cluster.*—Median 6 (9 on a water shoot).

*Flower cluster density.*—Is medium-dense.

*Diameter.*—20-35 mm.

*Length.*—30-50 mm.

*Color of peduncle.*—Yellow green 146C.

*Texture of peduncle.*—Is smooth.

*Color of pedicel.*—Yellow green 147C.

*Texture of pedicel.*—Is smooth.

Flowers:

*Length of bud.*—Medium (to 14 mm), bud shape tubular, oblong with acute apex.

*Bud color.*—Grayed red 181D (immature, tightly closed) to green 138C (calyx) with white NN155D corolla as it progresses to opening.

*Length of corolla*.—Tube medium (to 14 mm).
*Width of corolla*.—Tube medium (to 10 mm).
*Corolla aperture diameter*.—3-4 mm.
*Color of corolla*.—White NN155D.
*Anthocyanin coloration of corolla*.—Absent.
*Corolla ridges*.—Present.
*Protrusion of stigma*.—Absent, usually level with corolla apex.
*Fragrance*.—Weak.
*Shape*.—Urceolate.
*Abundance of pollen*.—High.
*Calyx (with sepals) diameter*.—6-7 mm.
*Calyx color*.—Green 138C.
*Productivity*.—Greater than 5 kg per season from 3-4 year old plants planted at 3.0 m×0.9 m density.
*Cold hardiness*.—'Ridley 3402' has not been grown in all environments including harsh winter environments. Cold tolerance is expected to be low.
*Chilling requirement*.—'Ridley 3402' has not been grown in all environments and is typically grown as an evergreen crop where chilling hours are not important. 'Ridley 3402' is classed as 'low chill', typical of Southern Highbush Blueberry varieties with an estimated chilling requirement of 200-250 hours (not tested).
*Leafing*.—Plants retain leaves year round (at Lindendale, NSW Australia) and 'Ridley 3402' is grown commercially as an evergreen crop. New leafing occurs in early to mid August at Lindendale, NSW Australia.

Fruit:

*Unripe fruit color intensity*.—Light.
*Unripe fruit color*.—Green 138A.
*Cluster density*.—Is dense.
*Diameter*.—Is medium (mean 20.3 mm).
*Weight*.—Medium (approximately 2.2 g).
*Shape*.—Oblate.
*Attitude of calyx*.—Erect.
*Diameter of calyx basin*.—Medium (mean 6 mm).
*Depth of calyx basin*.—Is medium to deep (to 2.0 mm).
*Intensity of bloom*.—Strong.
*Intensity of blue color of skin with bloom removed*.—Is very dark.
*Color of skin*.—Black 202A.
*Sweetness when ripe*.—Medium to high.
*Color of flesh when ripe*.—Grayed green 194A to 195A.
*Firmness when ripe*.—Firm.
*Acidity when ripe*.—Medium.
*Size of scar*.—Is small (1.0-1.5 mm).
*Storage quality*.—Good.
*Date of 50% maturity*.—Approximately 10$^{th}$ September at Lindendale, NSW Australia.
*Fruit development period*.—Approximately 55 days in protected cultivation at Lindendale, NSW Australia.

Seed:

*Seed color*.—Greyed orange 174B.
*Seed abundance in fruit*.—Medium.
*Seed size*.—1.6-1.8 mm long for fully developed seeds.

What is claimed is:

1. A new and distinct cultivar of *Vaccinium* hybrid plant named 'Ridley 3402', substantially as herein shown and described.

* * * * *